United States Patent
Petersen et al.

[11] Patent Number: 5,958,349
[45] Date of Patent: Sep. 28, 1999

[54] REACTION VESSEL FOR HEAT-EXCHANGING CHEMICAL PROCESSES

[75] Inventors: Kurt E. Petersen, San Jose; William A. McMillan, Cupertino; Gregory T. A. Kovacs, Stanford; Steven J. Young, Los Gatos, all of Calif.

[73] Assignee: Cepheid, Sunnyvale, Calif.

[21] Appl. No.: 08/808,325

[22] Filed: Feb. 28, 1997

[51] Int. Cl.⁶ .............................. F28D 8/04; G01N 21/29; G01N 21/47

[52] U.S. Cl. .......................... 422/198; 422/102; 422/68.1; 422/82.05; 422/82.08; 250/238; 356/246; 356/442

[58] Field of Search ................................ 422/102, 52, 58, 422/68.1, 82.05, 82.08, 198; 250/238; 356/246, 340, 349, 442

[56] References Cited

U.S. PATENT DOCUMENTS

| | | | |
|---|---|---|---|
| 4,265,538 | 5/1981 | Wertheimer et al. | 356/246 |
| 4,628,036 | 12/1986 | Scheepens et al. | 436/520 |
| 4,659,550 | 4/1987 | Schildknecht | 422/73 |
| 4,810,653 | 3/1989 | Helfer et al. | 435/316 |
| 4,902,624 | 2/1990 | Columbus et al. | 435/316 |
| 5,229,297 | 7/1993 | Schnipelsky et al. | 436/94 |
| 5,241,363 | 8/1993 | Garner | 356/326 |
| 5,244,637 | 9/1993 | Pratellesi et al. | 422/102 |
| 5,270,183 | 12/1993 | Corbett et al. | 435/91.2 |
| 5,281,516 | 1/1994 | Stapleton et al. | 435/3 |
| 5,316,732 | 5/1994 | Golukhov et al. | 422/102 |
| 5,346,672 | 9/1994 | Stapleton et al. | 422/102 |
| 5,460,780 | 10/1995 | Devaney, Jr. et al. | 422/99 |
| 5,504,007 | 4/1996 | Haynes | 435/285.1 |
| 5,527,510 | 6/1996 | Atwood et al. | 422/104 |
| 5,580,830 | 12/1996 | Nenyei et al. | 437/247 |
| 5,589,136 | 12/1996 | Northrup et al. | 422/102 |

FOREIGN PATENT DOCUMENTS

| | | |
|---|---|---|
| 0 436 995 A2 | 7/1991 | European Pat. Off. . |
| 0 545 736 A2 | 6/1993 | European Pat. Off. . |
| 0603411 | 6/1994 | European Pat. Off. . |
| 0 606 961 A1 | 7/1994 | European Pat. Off. . |
| 0 662 345 A1 | 7/1995 | European Pat. Off. . |
| 0 693 560 A2 | 1/1996 | European Pat. Off. . |
| 0723812 | 7/1996 | European Pat. Off. . |
| 19519015 | 9/1996 | Germany . |
| 05236932 | 9/1993 | Japan . |
| 07322873 | 12/1995 | Japan . |

OTHER PUBLICATIONS

Bever, M.B. (Encyclopedia of Materials Science and Engineering, Permagon Press, vol. 7, pp. 4916) 1986.

*Primary Examiner*—Hien Tran
*Assistant Examiner*—James Kennedy
*Attorney, Agent, or Firm*—Heller Ehrman White & McAuliffe

[57] ABSTRACT

A reaction vessel for holding a sample for a heat-exchanging chemical process has two opposing major faces and a plurality of contiguous minor faces joining the major faces to each other. The major and minor faces form an enclosed chamber having a triangular-shaped bottom portion. The ratio of the thermal conductance of the major faces to that of the minor faces is at least 2:1, and the minor faces forming the triangular-shaped bottom portion of the chamber are optically transmissive. The vessel also has a port for introducing a sample into the chamber and a cap for sealing the chamber.

11 Claims, 3 Drawing Sheets

5,958,349

REACTION VESSEL FOR HEAT-EXCHANGING CHEMICAL PROCESSES

This invention was made with Government support under contract DAAM01-96-C-0061 awarded by the U.S. Army. The Government has certain rights in the invention.

BACKGROUND OF THE INVENTION

This invention relates to reaction vessels useful for heat exchanging chemical processes, such as polymerase chain reaction (PCR).

Conventional PCR instrumentation typically consists of a block of aluminum having as many as ninety-six conical reaction tubes. The aluminum block is heated and cooled either by a Peltier heating/cooling apparatus, or by a closed-loop liquid heating/cooling system, flowing through channels machined into the aluminum block.

A fundamental element of the PCR process is thermal cycling, during which the temperature of the aluminum block is cycled between 60° C. and 95° C. as often as fifty times. Because of the large thermal mass of the aluminum block, heating and cooling rates are limited to about 1° C./sec, so that a fifty cycle PCR process may require two or more hours to complete.

The highest heating rate in commercial instruments is on the order of 5° C./second, and cooling rates are significantly less. With these relatively slow heating and cooling rates, it has been observed that some processes, such as PCR, are inefficient. For example, reactions may occur at the intermediate temperatures, creating unwanted and interfering DNA products, such as "primer-dimers" or anomalous amplicons, as well as consuming reagents necessary for the intended PCR reaction. Other processes, such as ligand binding, organic or enzymatic, when performed in non-uniform temperature environments, similarly suffer from side reactions and products that are potentially deleterious to the analytical method.

Another fundamental element of the PCR process is detection of the amplified DNA molecules. PCR-produced DNA has usually been detected in a second, complex, heterogeneous chemical hybridization step. New homogeneous DNA detection techniques, particularly ethidium bromide and polymerase chemistries based upon optical fluorescence, are providing PCR with new, highly specific, quantitative capabilities. One major advantage of this new chemistry is that accurate, quantitative data can be attained by monitoring optical fluorescence after each thermal cycle. In terms of practical implementation, the most important aspect is that complex, heterogeneous reactions are not required since the detection chemistry is performed in the PCR reaction chamber without further sample handling.

Preferred detection techniques for the analysis of DNA, RNA, and other biologicals are optical, typically fluorescence or chemiluminescence. Optimum optical sensitivity of fluorescence activity in fluid solutions can be attained by maximizing the optical sampling path-length of both the light beams exciting the fluorescence molecules and the emitted light that will be detected to generate the optical signal.

Instrumentation suitable for these newer processes, requiring "real-time" optical analysis after each thermal cycle, has only recently become available. Examples of these instruments include the Perkin Elmer 7700 (ATC) instrument and the Perkin Elmer 9600 instrument. Both instruments employ a 96-well aluminum block format, however, so that their heating and cooling rates are relatively slow. Optical fluorescence detection in the PE 7700 is accomplished by guiding an optical fiber to each of the ninety-six reaction sites. A central high power laser sequentially excites each reaction tube and captures the fluorescence signal through the optical fiber. Since all the reaction sites are sequentially excited by a single laser and fluorescence is detected by a single spectrometer and photomultiplier tube, complex beam-guiding and optical multiplexing are required.

An instrument from Idaho Technologies monitors each reaction tube in sequence as capillary sample carriers are rotated past heating and cooling sites and optical interrogation sites. This instrument is much simpler that the ATC, however, it is not easily configured for commercial, high throughput PCR diagnostic applications.

A third real-time PCR analysis system is the MATCI device developed by Dr. Allen Northrup et al., as disclosed in U.S. Pat. No. 5,589,136, incorporated herein by reference. This device uses a modular approach to PCR thermal cycling and optical analysis. Each reaction is performed in its own thermal cycling sleeve and each sleeve has its own associated optical excitation source and fluorescence detector. Using a new generation of blue LED's, simple optics and solid-state detectors, real-time data can be obtained from a compact, low-power module. Not only are the optics simple and efficient, but the low thermal mass of the thermal cycling sleeve allows the MATCI device to realize extremely fast thermal heating and cooling rates, up to 30° C./sec heating and 5° C./sec cooling.

For some diagnostic and environmental applications of PCR and other chemical detection methodologies, the volume of the tested unknown sample can be important. For example, in the detection of viruses in blood or urine, if a detection sensitivity of 10 virions/mL is necessary, then, a minimum fluid volume of at least 0.1 mL is required. (Statistically, 0.1 mL will only reliably detect about 30–40 virions/mL.) Therefore, the chemical analysis system must be designed to handle a wide range of fluid volumes, from nanoliters to milliliters.

For these reasons, optimization of the PCR process and similar biochemical reaction processes requires that the desired optimal reaction temperatures be reached as quickly as possible, spending minimal time at intermediate temperatures. Therefore the reaction vessels containing the reactants must be designed to optimize heating and cooling rates, to permit real time optical interrogation, and to accept various sample volumes.

SUMMARY

The present invention provides a reaction vessel for holding a sample for a heat-exchanging chemical reaction. The reaction vessel has two opposing major faces and a plurality of contiguous minor faces joining the major faces to each other. The major and minor faces form an enclosed chamber having a triangular-shaped bottom. The ratio of the thermal conductance of the major faces to that of the minor faces is at least 2:1, and the minor faces forming the bottom portion of the chamber are optically transmissive. The vessel also has a port for introducing a sample into the chamber and a cap for sealing the chamber.

DETAILED DESCRIPTION OF THE INVENTION

Figure 1A:
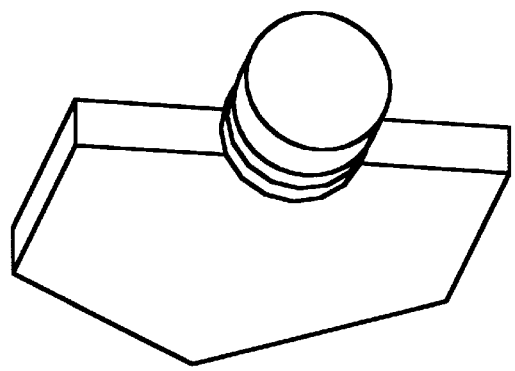
FIGS. 1a–1c show various views of a reaction vessel according to a first embodiment of the invention.

This invention provides a thin, flat reaction vessel having a chamber for holding a sample and incorporating optical surfaces on the sides of the chamber. The thin, flat shape contributes to optimal thermal kinetics by providing large uniform surfaces for thermal conduction, while at the same time the thin minor walls provide windows into the chamber such that the entire reaction sample can be optically interrogated. In addition, the thin, flat configuration is suitable for a wide range of reaction volumes.

The various embodiments of the reaction vessel have the following features: high surface-to-volume ratio for efficient heating/cooling; thin, low-mass walls; good shape retention and low surface texture to optimize mating with heating/cooling walls; moldable and bondable (if multiple pieces are required); designed to accommodate high thermal expansion coefficients to minimize thermal-induced mechanical stress during thermal cycling; chemically inert (no adsorption or reaction with reactants, intermediates, or products, no or minimal inactivation of enzymes by surface active means, and compatible with glycerol); high optical clarity for efficient interrogation (required for excitation and emission windows); long excitation optical path lengths; maximized offset between excitation and emission detection windows; no or minimal light coupling between excitation and detection devices; precise mating of major walls with module heating/cooling surfaces; port for introducing sample and reagents; means to preclude or minimize refluxing during cycling; efficient removal of air during filling and capping; and sealing of the reaction mixture from external environment.

The reaction vessel is molded of plastic and has a chamber formed by major walls, sidewalls, and optical windows. An insert which will fill the top of the chamber and provide the two upper minor sides is either bonded or preferably press-fitted into the chamber. The insert also provides the channel, port, and cap attachment means.

Alternatively, a separate molded optical window piece offers the flexibility to select more than one material for the chamber. Materials with optimal thermal characteristics may be different from those with optimal optical characteristics. The optical window is press-fitted or bonded into the bottom of the vessel.

A reaction vessel in which the major and minor faces are fabricated from the same material requires that the total surface area of the major surfaces be at least about twice that of the total surface area of the minor surfaces to provide the desired thermal conductance ratio of 2:1. On the other hand, if the faces are made of different materials, it is possible to modify the geometry from that shown since major faces comprised of materials with high thermal conductivity could be combined with minor faces of low thermal conductivity. The faces may be fabricated from glass or plastics selected from the group consisting of polyacrylics, polyamides, polycarbonates, polyesters, and vinyl polymers, or any combination thereof. Polycarbonates are preferred for the optically transmittive faces.

The minor faces forming the triangular shaped bottom may be offset at an angle selected to maximize the detection process. In one embodiment, the optical faces are offset about 90° from each other. One or more light transmissive elements may be present on the bottom-forming minor faces. The optical elements may be designed, for example, to maximize the total volume of solution which is illuminated by an LED fluorescence excitation source, to focus an optical excitation source on a specific region of the reaction chamber, or to collect as much fluorescence signal from as large a fraction of the reaction chamber volume as possible. In addition, gratings for selecting specific wavelengths, filters for allowing only certain wavelengths to pass, and multiple lenses or filters optimized for multiple excitation sources or detectors may be used. In another embodiment, the opposite face may be optimized to collect and focus the maximum percentage of emitted fluorescence signal from the solution to an array of photodetectors. Alternatively, the faces may be simple, clear, flat windows serving as optically transmissive windows.

The reaction vessels may be fabricated in various ways. They can be injection molded in one piece, or they can be molded in several pieces and bonded together. There are several advantages to the two-piece design and manufacturing approach. First, the optical features of the device are separated from the fluidic features; both components can be designed and optimized independently. Second, the primary optical component can be fabricated from a different material than the primary fluidic component. Third, the major surfaces may be fabricated from a different material than the minor surfaces. For example, the V-shaped optical window/lens component could be molded from polycarbonate, which has good optical transparency, while the fluidic chamber could be molded from polypropylene, which is inexpensive and is known to be compatible with the sensitive PCR reaction. Both pieces can be bonded together in a secondary step.

The vessel is provided with sealing means which may be a snapon cap, a screwtop, or other specialized closure as needed for the selected analytical protocol. The vessel may be designed to contain volumes from nanoliters to milliliters, depending upon the desired use. Preferably, the volume of the chamber is from about 1 to about 1000 microliters, more preferably from about 10 to about 100 microliters.

Figure 1B:
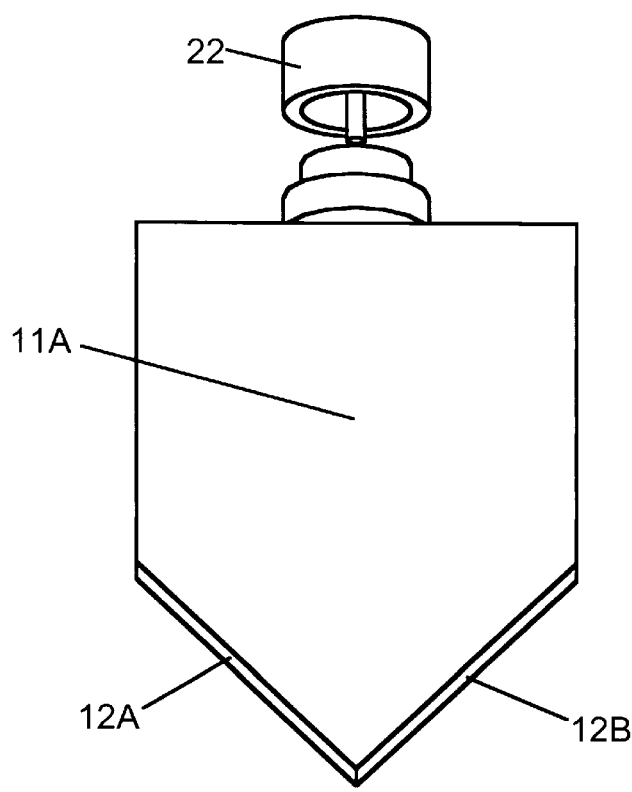
Figure 1C:
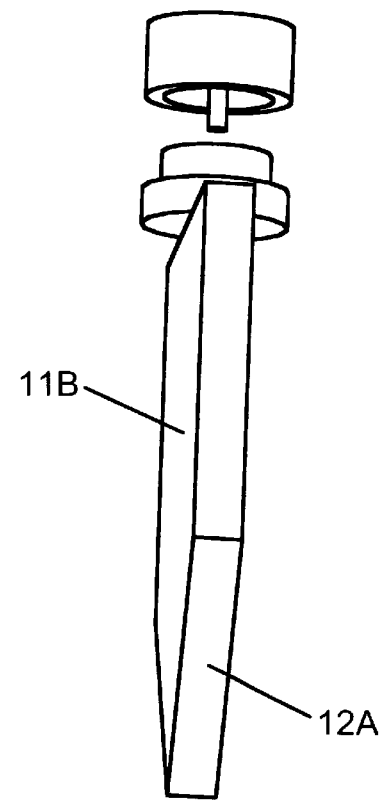
Figure 2:
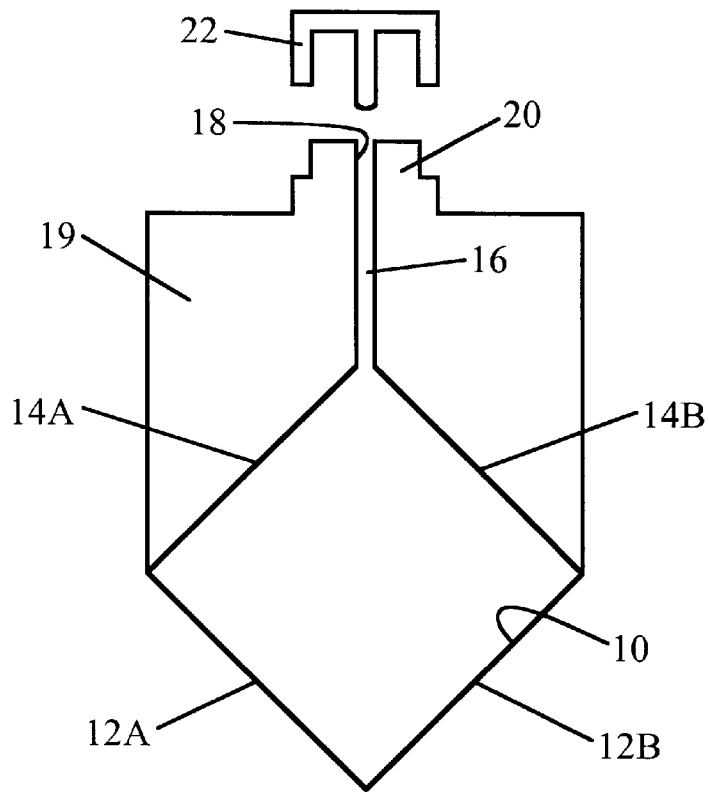
FIG. 2 shows a cross sectional view of the vessel of FIGS. 1a–c.

FIGS. 1–2 show a reaction vessel according to a first embodiment of the present invention. The vessel has a chamber 10 bounded by two major faces 11A, 11B and four minor faces 12A, 12B, 14A, and 14B. The two major faces 11A, 11B are of low thermal mass, and provide very large surfaces for rapid heating and cooling of a sample in chamber 10. Of the four minor faces, the bottom two faces 12A, 12B comprise the optical windows. These are offset by 90 degrees, with one window serving as a light excitation entry port and the second for emitted light detection. Other angles may be selected. The other two minor faces 14A, 14B are located within the interior of the chamber and complete the containment geometry in conjunction with the two major faces and the two optical windows.

As shown in FIG. 2, an insert 19 fills the top of the vessel and provides the two upper minor sides 14A, 14B. The insert is either bonded or preferably press-fitted into the vessel. The insert also provides a channel 16, a port 18, and a cap attachment means 20. The channel 16 connects the port 18 to the chamber 10 and provides a means for adding liquids and removing air. It allows access of a pipette tip through the channel from the outside into the interior of the chamber and down to the bottom to enable bottom-up filling. The external terminus of the channel is designed to accept a cap 22 and optionally provide an area to hold overfilled reagents and purged air. The cap provides a means for sealing the port after filling to provide a barrier between the thermally controlled interior reaction volume and the non-thermally controlled exterior. The bottom portion of the chamber 10 is pointed to allow easier filling, reducing bubble formation.

Figure 3:
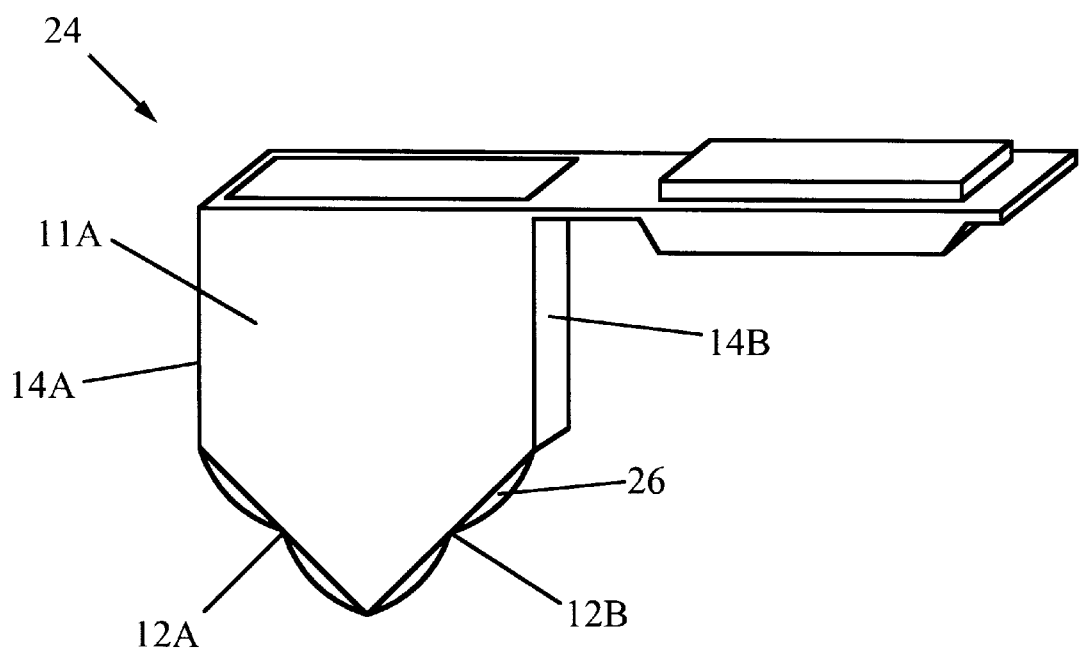
FIG. 3 shows a reaction vessel according to a second embodiment of the invention.

FIG. 3 shows a reaction vessel 24 according to a second embodiment of the invention. The bottom faces 12A, 12B are not necessarily planar. They can be molded to provide one or multiple lenses, colored to provide filtering functions, molded to provide optical grating surfaces, etc. FIG. 3, for example, shows two lenses 26 on each of the minor faces 12A, 12B directly molded into the surfaces.

Figure 4:
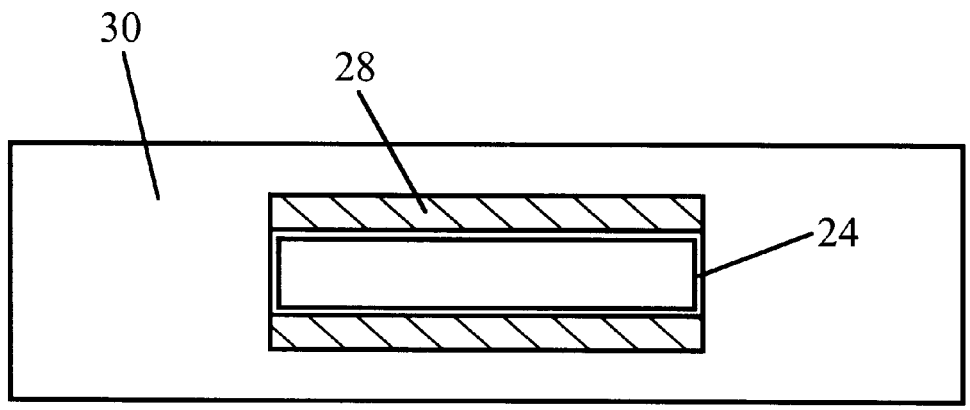
FIG. 4 shows a cross sectional view of the vessel of FIG. 3 in contact with heating elements and surrounded by a cooling chamber.
Figure 5:
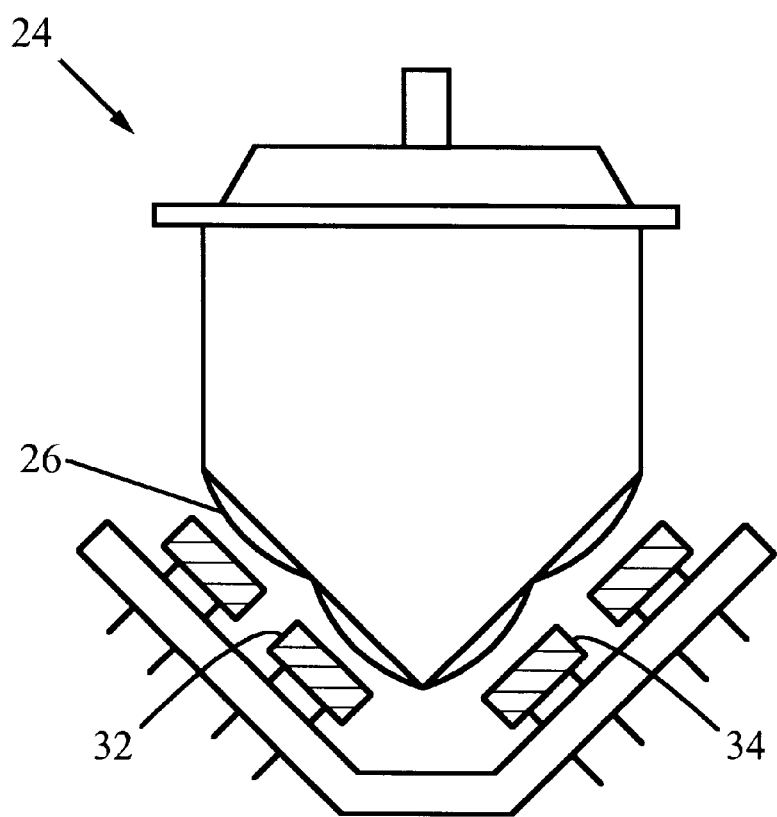
FIG. 5 shows a side view of the vessel of FIG. 3 with an arrangement of fluorescence sources and detectors.

FIG. 4 is a cross-sectional top view of the reaction vessel 24 in intimate contact with heating elements 28 and surrounded by cooling chamber 30. FIG. 5 shows the reaction vessel 24 configured with LED sources 32 and detectors 34. The vessel has molded lenses 26.

What is claimed is:

1. A reaction vessel comprising:
   a) two opposing major faces for mating with heating or cooling surfaces;
   b) a plurality of minor faces, wherein each of the minor faces joins the major faces to each other to form a chamber having a triangular-shaped bottom portion;
   c) a port for introducing the sample into the chamber; and
   d) means for sealing the port;
   wherein the ratio of the thermal conductance of the major faces to that of the minor faces is at least 2:1, and the minor faces forming the triangular-shaped bottom portion are optically transmissive.

2. The reaction vessel of claim 1, wherein the ratio of the total surface area of the major faces to the total surface area of the minor faces is at least 2:1.

3. The reaction vessel of claim 1, wherein the minor faces forming the bottom portion of the chamber are angularly offset from each other by an angle of about 90°.

4. The reaction vessel of claim 1, further comprising an optical element on at least one of the minor faces forming the bottom portion of the chamber.

5. The reaction vessel of claim 4, wherein the optical element comprises a lens molded into the surface of the minor face.

6. The reaction vessel of claim 1, further comprising at least one optical element on each of the minor faces forming the bottom portion of the chamber.

7. The reaction vessel of claim 1, wherein each of the minor faces forming the bottom portion of the chamber has at least one lens molded into its surface.

8. The reaction vessel of claim 1, wherein the minor faces forming the bottom portion of the chamber are fabricated from a different material than the other faces.

9. The reaction vessel of claim 1, wherein the chamber has a volume capacity in the range of 10 to 100 microliters.

10. The reaction vessel of claim 1, wherein the minor faces forming the top portion of the chamber are provided by an insert fitted into the vessel.

11. The reaction vessel of claim 10, wherein the insert further defines the port and a channel connecting the port to the chamber.

\* \* \* \* \*